(12) United States Patent
Freier et al.

(10) Patent No.: US 7,445,624 B2
(45) Date of Patent: Nov. 4, 2008

(54) ENDOSCOPIC SAMPLE TAKER FOR CARTILAGE MATERIAL

(75) Inventors: Mark Freier, Oberderdingen (DE); Eberhard Körner, Bretten (DE); Helmut Heckele, Knittlingen (DE)

(73) Assignee: Richard Wolf GmbH, Knittlingen (DE)

( * ) Notice: Subject to any disclaimer, the term of this patent is extended or adjusted under 35 U.S.C. 154(b) by 805 days.

(21) Appl. No.: 10/002,523

(22) Filed: Nov. 2, 2001

(65) Prior Publication Data

US 2002/0040228 A1 Apr. 4, 2002

(30) Foreign Application Priority Data

Nov. 2, 2000 (DE) ................................. 100 54 265

(51) Int. Cl.
*A61B 17/32* (2006.01)
(52) U.S. Cl. ..................................................... 606/167
(58) Field of Classification Search ................. 606/160, 606/167; 600/570, 571
See application file for complete search history.

(56) References Cited

U.S. PATENT DOCUMENTS

| 4,569,131 A | * | 2/1986 | Falk et al. ..................... 30/251 |
|---|---|---|---|
| 4,651,752 A | | 3/1987 | Fuerst |
| 4,763,669 A | * | 8/1988 | Jaeger .......................... 600/564 |
| 4,800,896 A | | 1/1989 | Jalowayski |
| 4,926,877 A | | 5/1990 | Bookwalter |
| 4,953,559 A | * | 9/1990 | Salerno ....................... 600/564 |
| 5,318,528 A | * | 6/1994 | Heaven et al. ............ 604/95.01 |
| 5,385,570 A | * | 1/1995 | Chin et al. .................. 606/170 |
| 5,683,406 A | | 11/1997 | Altobelli et al. |
| 6,030,400 A | | 2/2000 | Johnson |

FOREIGN PATENT DOCUMENTS

| DE | 1 855 179 | 7/1962 |
|---|---|---|
| DE | 43 28 855 | 1/1995 |
| FR | 2 450 597 | 3/1980 |
| WO | WO 97/11646 | 4/1997 |

* cited by examiner

*Primary Examiner*—Todd E. Manahan
*Assistant Examiner*—Tuan V Nguyen
(74) *Attorney, Agent, or Firm*—Cohen Pontani Lieberman & Pavane LLP

(57) ABSTRACT

The sample taker comprises a hollow shank with a scoop fixedly connected at its distal end, a handling means provided at the proximal end of the 20 hollow shank and an actuation mechanism. An actuation rod is axially movable in the hollow shank and connectable to the actuation mechanism. A covering is allocated in the trough of the scoop. The covering is fastened to a distal end of the actuation rod and displaceable forwards and backwards.

11 Claims, 3 Drawing Sheets

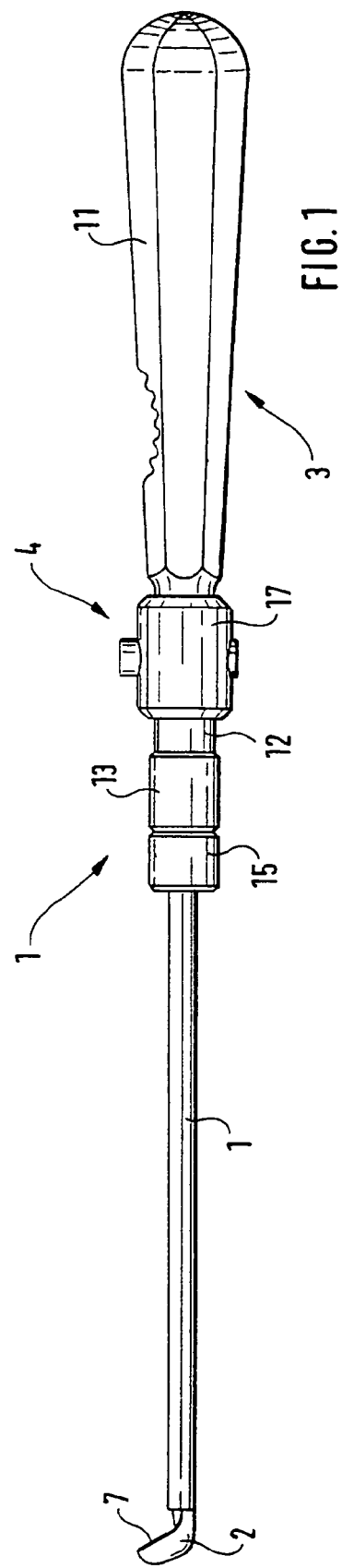
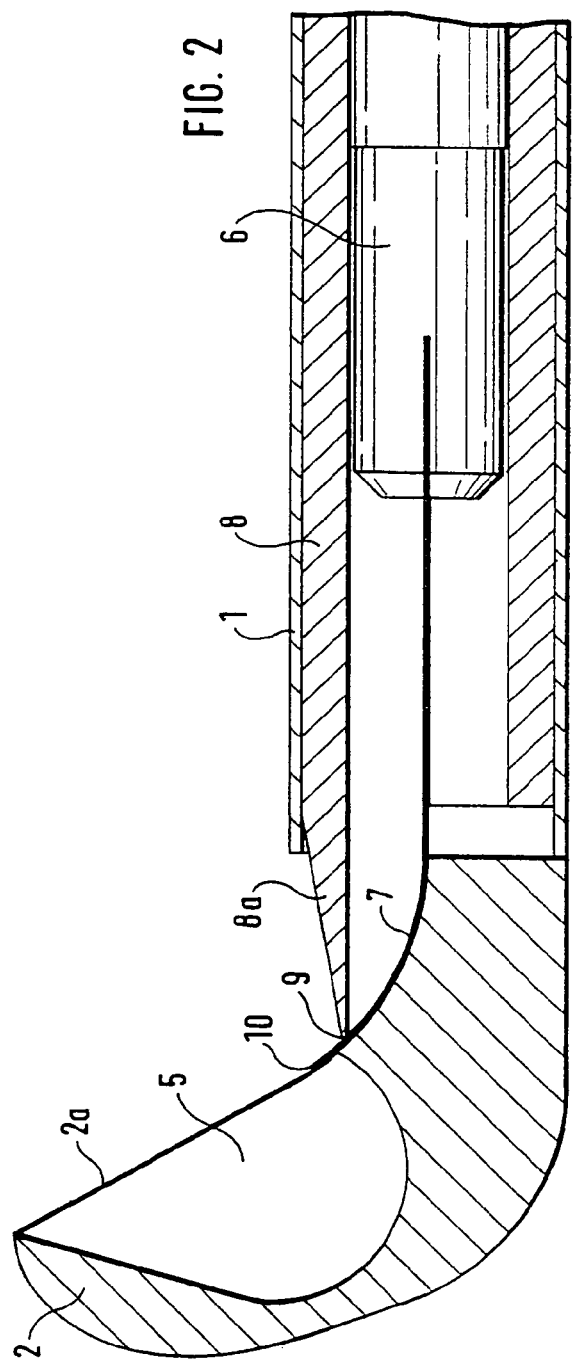

ENDOSCOPIC SAMPLE TAKER FOR CARTILAGE MATERIAL

BACKGROUND OF THE INVENTION

1. Field of the Invention

The invention relates to an endoscopic sample taker for in particular cartilage material.

2. Description of the Related Art

Such a sample taker is described in the German utility model 1 855 179. It consists of a hollow shank with an actuation rod axially adjustable therein, of a scoop pivotably arranged at the distal end of the hollow shank and of a scissor-like handle arranged at the proximal end of the hollow shank. This handle comprises a stationary grip part which is rigidly fastened on the hollow shank, and a movable grip part which is pivotably connected to the unmovable grip part and engages the proximal end of the actuation rod. By actuating the movable grip part the scoop by way of the actuation rod is pivoted with respect to the hollow shank so that by way of pivoting forward and back the scoop, cartilage tissue, in particular of human joints, may be released by way of abrading. The abraded cartilage particles are removed from the body by rinsing out and are complicated and difficult to extract from the rinsing fluid in order to cultivate new and reimplantable cartilage mass from this. Furthermore it has proven to be advantageous to remove the desired cartilage particles with the scoop alone from the joint or from another diseased cartilage region of a patient because the abraded cartilage particles on withdrawing the sample taker from the body cavity concerned are again to a great extent lost. A further disadvantage of this known sample taker lies in the fact that the scoop for the abrading procedure must be set considerably transversely and thus on account of its construction and for carrying out its function it requires considerable space in the body cavity of the joint or likewise.

Furthermore there are known biopsy forceps with one or two pivotable, hollow jaw parts for the secure removal of tissue samples. The jaw parts are located at the distal end of the hollow shank on whose proximal end there is provided a handle for actuating the jaw parts. These forceps are suitable essentially only for removing soft tissue and not for cartilage tissue or likewise, since this is considerably harder. Furthermore these jaw parts for carrying out their function also require much space because they must be spread apart transverse to the longitudinal direction of the hollow shank.

BRIEF SUMMARY OF THE INVENTION

The object of the invention lies in improving an endoscopic sample taker for cartilage material which with a low distal space requirement ensures a secure and quick removal of cartilage material from in particular human body cavities.

An endoscopic sample taker according to an embodiment of the present invention includes a hollow shank with a distal end and proximal end. A scoop defining a trough is fixedly connected to the distal end of the hollow shank and a handle with an actuating mechanism is connected to the proximal end of the hollow shank. An actuating rod is inserted in the hollow shank and is axially movable therein. The proximal end of the actuating rod is releasably connectable to the actuating mechanism. A covering for the trough of the scoop is connected to the actuating rod at a distal end of the actuating rod so that the covering is displaceable with the actuating rod between a closure position and an open position. The open position of the covering allows ingress of the cartilage material to said trough and the closure position prevents loss of the cartilage material from the trough.

With this solution cartilage material may be removed without loss thereof in a secure and rapid manner from a cartilage location, e.g. from a knee joint of a patient in order to be able to be used for obtaining or cultivating new cartilage cell material which then is reimplanted at a damaged cartilage location in the body of the patient. After healthy cartilage material by way of abrading has reached the trough of the scoop from the desired cartilage location the trough by way of advancing the covering according to the invention is closed so that separated-off cartilage tissue on withdrawing the sample taker from the body of the patient may not get lost. A further advantage of the sample taker according to the invention lies in the fact that the covering for the trough of the scoop is arranged at the distal end of the sample taker in an extremely space-saving manner and by way of this demands practically very little space particularly as it is located in the non-operational position in the retracted position in the hollow shank. Furthermore it is advantageous that the covering is to be simply manufactured with very low costs.

In one advantageous embodiment of the sample taker according to the invention the covering for the trough of the scoop consists or a metal tongue. In the case that the scoop is bent back at a certain angle with regard to the hollow shank, the covering consists of flexible material. With this it is advantageous that in the hollow shank there is provided an axially movable holding-down device in order to hold the covering on the scoop in the closed position.

BRIEF DESCRIPTION OF THE DRAWINGS

The invention is hereinafter described in more detail by way of one embodiment example shown in the accompanying drawings in which:

FIG. 1 is a lateral view of the sample taker according to an embodiment of the present invention, FIG. 2 is an axial section through the distal end region of the sample taker of FIG. 1;

DETAILED DESCRIPTION OF THE INVENTION

Figure 3:
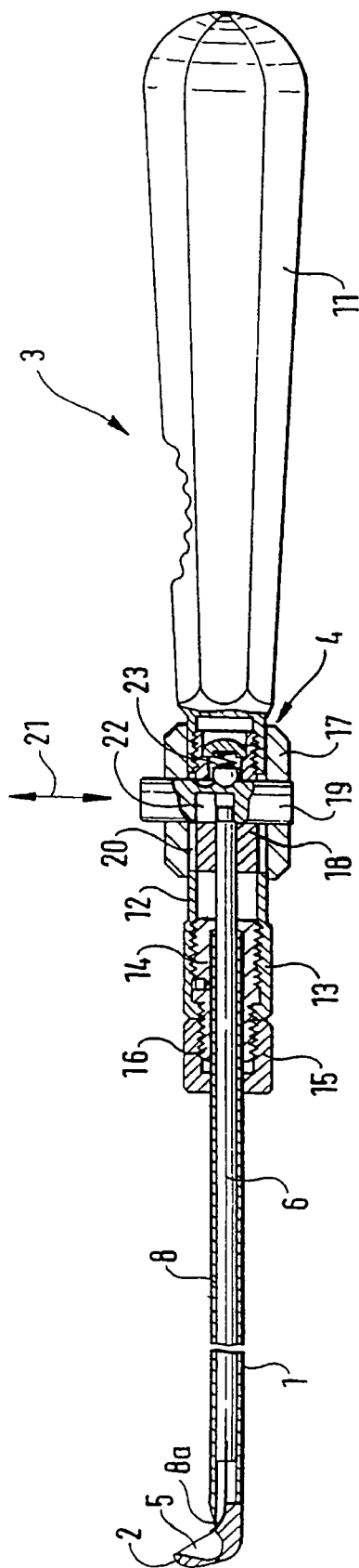
FIG. 3 is a part axial section through the sample taker according to FIG. 1.
Figure 4:
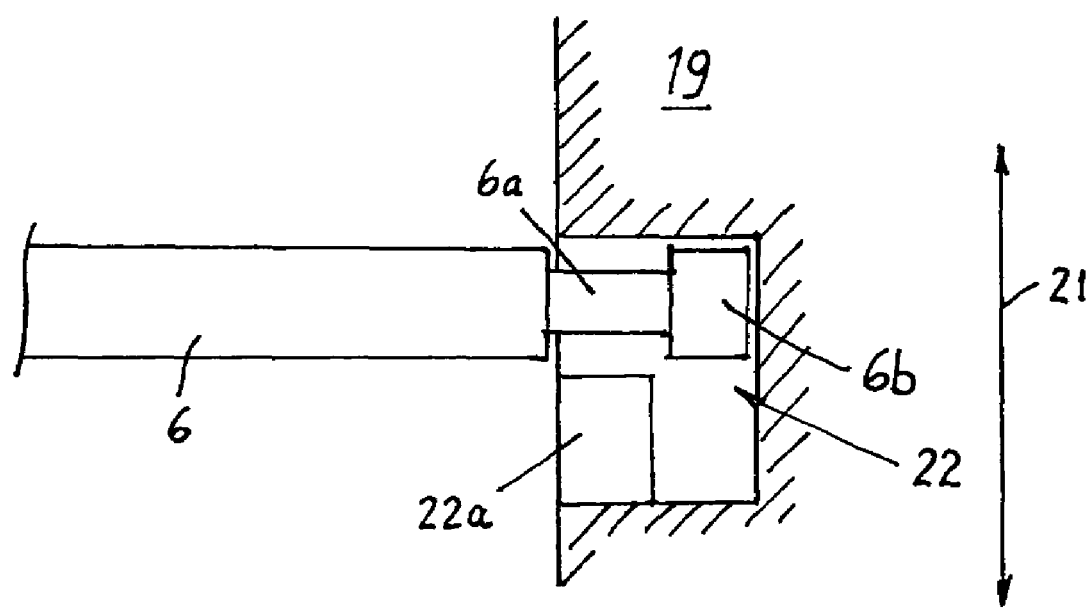
FIG. 4 is a sectional view of the releasable connection of the actuating rod of the sample take of FIG. 3.

The sample taker 100 in FIG. 1 according to an embodiment of the present invention comprises a hollow shank 1 with a scoop 2 which is rigidly and unreleasably fastened on a distal end of the hollow shank, and a handling means 3 with an actuating mechanism 4. The scoop 2 comprises a spoon-like or shell-like trough 5 for collecting therein cartilage material, bone material or similar hard material that is extracted from a body cavity of a living being, such as a patient, this material being obtained by way of abrading. For the purpose of abrading, the scoop has a sharp edge 2a. In the hollow shank 1 there is located an actuation rod 6 on whose distal end there is fastened a tongue-shaped covering 7 for the trough of the scoop 2 (FIG. 2). The material for the covering 7 is preferably thin metal. The covering may have a strip-like form and in its covering section have a circumferential shape which corresponds to the circumferential shape or essentially to the circumferential shape of the trough 5. At the same time it is essential that the trough 5 is sufficiently covered by the covering 7 so that the gained cartilage material on retracting the sample taker 1 from the body cavity of the patient is not lost.

The scoop 2 may extend coaxially to the hollow shank 1. It is however also possible to provide the scoop running at a certain angle with respect to the hollow shank 1, as this is shown in FIGS. 1, 2 and 3. In this case the covering 7 consists of a bending-elastic material so that it automatically bends and adapts to the oblique running of the edge 2a of the scoop 2 when the actuation rod 6 is advanced. In order to ensure a secure guiding of the covering 7 on the scoop 2 it is advantageous to provide a holding-down device 8 which comprises a distal continuation 8a which with the scoop 2 determines a gap 9 for guiding the covering 7. The holding-down device 8 may consist of a cylinder section unrealeasably fastened in the shank 1 or may form a part of the shank 1. The actuation rod 6 with the covering 7 for its axial displacement is guided by the holding-down device. With the continuation 8a of the holding-down device 8 it is also achieved that the covering 7 pushed over the trough 5, over the scoop 2 is held in the closure position.

In a further advantageous embodiment the front edge 10 of the covering 7 may be formed as a cutter 10 in order to simplify a separation of cartilage tissue or likewise.

For the axial actuation of the actuation rod 6 with the covering 7 there is provided an inclined handling means. This means is not the subject-matter of the invention and is therefore described only briefly.

The hollow shank 1 with the scoop 2 and the actuation rod 6 with the covering 7 form a dismountable construction unit which is releasably connected to the handling means 3. The handling means 3 comprises a hand grip 11 with a distal sleeve section 12 as a component of the actuating mechanism 4. Onto the sleeve section 12 there may be screwed a screw sleeve 13 in order to fasten the proximal end part 14 of the holding-down device 8 in the sleeve section 12. The screw sleeve 13 may alternatively be formed as one unitary part with the sleeve section 12 as shown in FIG. 3. Furthermore a union nut 15 is screwable onto the proximal end of the end component 14 in order to fasten the hollow shank 1 on the handling means 3.

The actuating mechanism 4 comprises further an external cylindrical ring 17 arranged axially displaceable on the sleeve section 12 and an inner cylindrical ring 18 rigidly fastened within the sleeve section 12 on the actuation rod 6, as well as a fastening bar 19. The bar 19 passes through the rings 17 and 18 as well as an axial elongate hole 20 of the sleeve section 12. Furthermore the bar 19 is adjustable according to the double arrow 21.

The bar 19 has furthermore a suitable receiver 22 for the positive-fitting insertion of the proximal end of the actuation rod 6. Furthermore in the inner cylindrical ring 18 of the mechanism 4 there is provided a ball-lock formation 23 in order to fix the bar 19 in the locking position and in a release position. In FIG. 3 the ball-lock formation 23 is shown in its locking position.

For the axial actuation of the covering 7 the outer ring 17 is actuated in the axial direction, i.e. according to the course of the hollow shank 1. Thus also the actuation rod 6 is axially moved so that the covering 7 may be pushed over the trough 5 of the scoop 2. In order to again open the trough the outer ring 17 is again pushed back, i.e. proximally.

The invention claimed is:

1. An endoscopic sample taker for collecting a sample of cartilage material, comprising:
   a hollow shank having a distal end and a proximal end;
   a scoop fixedly connected to said distal end of said hollow shank and defining a spoon-shaped trough having an opening and a closed end;
   a handling means connected at said proximal end of said hollow shaft and having an actuation mechanism;
   an actuating rod having a distal end and a proximal end axially movable in said hollow shank, said proximal end of said actuating rod releasably connectable with said actuation mechanism; and
   a covering comprising a tongue having a longitudinal length with a first end fastened proximate said distal end of said actuating rod and a second distal end, said tongue being slidably adjustable so that said tongue slides along a longitudinal length of said tongue in response to axial adjustment of said actuating rod to an adjusted position between a closure position and an open position, wherein said open position of said tongue allows ingress of the cartilage material to said trough and said closure position covers said trough to prevent loss of the cartilage material from said trough, said adjusted position being maintained without external force on said actuating rod.

2. The endoscopic sample taker of claim 1, wherein said trough comprises an edge defining a shape of said opening of said trough, said tongue sufficiently covering said trough in said closed position so that an entire sample within the volume defined between said opening and said closed end is prevented from leaving said trough.

3. The endoscopic sample taker of claim 1, further comprising a holding-down device for guiding said tongue during the displacement thereof along the longitudinal length of said tongue and holding said tongue at said closure position.

4. The endoscopic sample taker of claim 1, wherein said scoop comprises an edge forming said trough and said edge is inclined at an angle relative to a longitudinal axis of said hollow shank such that a retrograde inclination is exhibited by said edge of said scoop.

5. The endoscopic sample taker of claim 4, wherein said tongue is made of a bendable elastic material.

6. The endoscopic sample taker of claim 1, wherein said tongue comprises a front cutting edge for facilitating separation of the sample of cartilage material.

7. The endoscopic sample taker of claim 1, wherein a volume defined between said opening and said closed end of said trough of said scoop is separated from a volume defined by said hollow shank such that the volume defined by said trough is not in direct communication with the volume defined by said hollow shank.

8. The endoscopic sample taker of claim 1, wherein an entire volume defined between said opening and said closed end of said trough of said scoop is arranged distally from said distal end of said hollow shank by an axial distance.

9. An endoscopic sample taker, comprising:
   a hollow shank having a distal end and a proximal end;
   a scoop fixedly connected to said distal end of said hollow shank and defining a spoon-shaped trough having an opening and a closed end;
   a handling means connected at said proximal end of said hollow shaft and having an actuation mechanism;
   an actuating rod having a distal end and a proximal end axially movable in said hollow shank, said proximal end of said actuating rod releasably connectable with said actuation mechanism; and
   a covering comprising a tongue having a longitudinal length with a first end fastened proximate said distal end of said actuating rod and a second distal end, a position of said tongue being adjustable along a longitudinal length of said tongue via said actuating rod to an adjusted position between a closure position and an open position, wherein said open position of said tongue allows ingress of the cartilage material to said trough and said closure position covers said trough to prevent loss of the cartilage material from said trough, said adjusted position being maintained without external force on said actuating rod, wherein said tongue comprises a thin strip having a longitudinal length, wherein the position of said covering is adjustable by axially displacing the thin strip along the longitudinal length of the thin strip so that the strip moves across the opening defined by said spoon-shaped trough in response to said actuating rod.

10. The endoscopic sample taker of claim 9, further comprising a holding-down device for guiding said thin strip during the displacement thereof and holding said tongue at said closure position.

11. The endoscopic sample taken of claim 1, wherein said actuating mechanism comprises a sleeve connected to said handling means, an external ring axially displaceably arranged outside said sleeve, an inner ring arranged inside said sleeve, and a fastening bar passing through said inner and external rings, said actuating rod being actuatable by axial movement of said outer ring.

* * * * *